United States Patent
Bransgrove (10) Patent No.: US 10,267,812 B2
(45) Date of Patent: Apr. 23, 2019

(54) TAPE POSITIONING SYSTEM AND METHOD

(71) Applicant: Brandon Bransgrove, New South Wales (AU)

(72) Inventor: Brandon Bransgrove, New South Wales (AU)

( * ) Notice: Subject to any disclaimer, the term of this patent is extended or adjusted under 35 U.S.C. 154(b) by 234 days.

(21) Appl. No.: 15/305,044

(22) PCT Filed: Oct. 19, 2015

(86) PCT No.: PCT/AU2015/050643
§ 371 (c)(1),
(2) Date: Oct. 18, 2016

(87) PCT Pub. No.: WO2015/061622
PCT Pub. Date: Apr. 28, 2016

(65) Prior Publication Data
US 2017/0192026 A1 Jul. 6, 2017

(30) Foreign Application Priority Data
Oct. 19, 2014 (AU) ................. 2014904214

(51) Int. Cl.
*G01N 35/00* (2006.01)
*G01N 21/86* (2006.01)
(Continued)

(52) U.S. Cl.
CPC ... *G01N 35/00009* (2013.01); *B65H 23/1806* (2013.01); *G01D 5/145* (2013.01);
(Continued)

(58) Field of Classification Search
CPC combination set(s) only.
See application file for complete search history.

(56) References Cited

U.S. PATENT DOCUMENTS 3,526,480 A 9/1970 Findl et al.
4,954,319 A 9/1990 Koizumi et al.
(Continued)

FOREIGN PATENT DOCUMENTS

WO 2014/122324 A1 8/2014

OTHER PUBLICATIONS

Feb. 1, 2016 Search Report issued in International Patent Application No. PCT/AU2015/050643.
(Continued)

*Primary Examiner* — Brian R Gordon
(74) *Attorney, Agent, or Firm* — Oliff PLC (57) ABSTRACT

A method of positioning a tape that includes determining an estimated position of a test element on the tape and rotating a spool that carries the tape in order for the test element to be positioned at a reading station. The estimated position of the test element is determined based on detected rotation of the spool, which can be measured at any shaft in the drive train. Also disclosed is a testing process for testing a sample deposited on a test element of a tape held on a spool of a cassette, a system for determining an estimated position of a test element on a tape which is carried by a cassette, and a memory storage medium associated with an in vitro diagnostic test cassette.

25 Claims, 10 Drawing Sheets

(51) Int. Cl.
- *G01N 21/84* (2006.01)
- *G01N 33/487* (2006.01)
- *G01D 5/14* (2006.01)
- *G01D 5/244* (2006.01)
- *G08B 5/22* (2006.01)
- *G08B 3/10* (2006.01)
- *B65H 23/18* (2006.01)

(52) U.S. Cl.
CPC ......... *G01D 5/244* (2013.01); *G01N 21/8483* (2013.01); *G01N 21/86* (2013.01); *G01N 33/48764* (2013.01); *G01N 33/48771* (2013.01); *G01N 35/00693* (2013.01); *G01N 35/00732* (2013.01); *G08B 3/10* (2013.01); *G08B 5/22* (2013.01); *B65H 2557/61* (2013.01); *G01N 2035/009* (2013.01)

(56) References Cited

U.S. PATENT DOCUMENTS

| | | |
|---|---|---|
| 6,316,264 B1 | 11/2001 | Corey et al. |
| 8,282,893 B2 | 10/2012 | Schosnig et al. |
| 8,313,696 B2 | 11/2012 | Seidenstricker et al. |
| 8,888,942 B2 * | 11/2014 | Dagenbach ............ B31D 1/021 156/230 |
| 2006/0216817 A1 * | 9/2006 | Hoenes ............... A61B 5/14532 435/287.2 |
| 2007/0020143 A1 | 1/2007 | Seidenstricker et al. |
| 2010/0228518 A1 * | 9/2010 | Shakespeare ........ D21G 9/0009 702/155 |
| 2012/0010489 A1 * | 1/2012 | Miltner .............. G01N 21/8483 600/365 |
| 2012/0273112 A1 * | 11/2012 | Dagenbach ............ B31D 1/021 156/64 |
| 2014/0242705 A1 * | 8/2014 | Chang ................ A61B 5/14532 436/44 |
| 2015/0320346 A1 * | 11/2015 | Chen ................ A61B 5/150022 600/365 |
| 2017/0146437 A1 * | 5/2017 | Calatzis .................. G01N 1/30 |

OTHER PUBLICATIONS

Feb. 1, 2016 Written Opinion issued in International Patent Application No. PCT/AU2015/050643.

Jul. 1, 2016 International Preliminary Report on Patentability issued in International Patent Application No. PCT/AU2015/050643.

\* cited by examiner

TAPE POSITIONING SYSTEM AND METHOD

FIELD

The invention relates to a tape positioning system and method, particularly but not exclusively for positioning a tape of a cassette used in an in-vitro-diagnostic analysis device.

BACKGROUND

Body fluid samples such as blood, plasma, urine, interstitial fluid etc may be analyzed for various components or properties, such as glucose, cholesterol, pathogens, drugs of abuse, coagulation, hematocrit etc. For testing purposes, a body fluid sample is applied to a test element containing reactive ingredients. A reaction occurs and a result is produced.

Tests elements may be supplied in multiple numbers arranged along a carrier tape, in housings commonly referred to as cassettes. Test cassettes with two chambers, one containing unused test material and the other for storage of used test material are known for use in laboratory analysers, as well as portable analysers.

Test elements located on carrier tapes must be drawn out of a supply chamber to a reading station where a liquid sample is applied and analysed. Each test element is spaced apart from the adjacent element by sufficient distance to enable a test element to be at the reading station while the following element remains protected in the supply chamber.

It is possible to the draw the tape out of the supply chamber by motorised, mechanical or manual means. In all cases, it is necessary to ensure the test element is correctly positioned over the reading station before a sample is applied and analysed, in order to avoid inaccurate results or an error message.

In the case of manually driven tape cassettes, it may be possible for the user to simply watch the test element appear from the supply chamber and continue winding until it is over the reading station. In practice, the user may wind the test tape too far if winding quickly or if distracted during the winding. As the tape can only be wound one way this would mean the test is wasted and another test element would need to be used.

In the case of an automated system, the motor needs to be turned on and off at the correct moment to ensure the element is located over the reading station. To achieve this, the analyser device must utilise a positioning system. Such a system requires a sensing method. This may be optical, inductive, mechanical, capacitive, magnetoresistive or hall effect for example. In selecting a sensing option for a handheld battery operated medical device, cost, reliability, power consumption and resolution are extremely important factors to be considered.

The prior art contains examples of several positioning systems. U.S. Pat. No. 3,526,480 Findl et al., describes a carrier tape with sprocket holes to index positions. Multi-layered porous elements impregnated with appropriate reagents are bonded along the carrier tape. Information is encoded on the carrier tape adjacent to each reaction site in the form of magnetic coding or punch holes. This information identifies the sample being analysed, the test being run and even the result of the analysis, but does not assist in the positioning. Creating sprocket holes is impractical with narrow, thin foil carrier tapes (similar in dimensions to audio tape) which are preferred in portable devices.

U.S. Pat. No. 4,954,319 Koizumi et al., describes a positioning system for a long film test cassette that has either colorimetric analytical test elements or electrode analytical test elements laminated to a carrier tape. A roller is pressed directly against the tape to measure the movement of the tape. To avoid tape slippage the roller perforates the tape with needle protrusions or has a rasp like surface that bites into the tape. The roller can become contaminated by sample if down line from the sample application site. Alternatively if the roller is situated before the sample application site it can damage the test elements.

U.S. Pat. No. 8,313,696 Seidenstricker et al., proposes a tape positioning system that uses optical sensing of a plurality of positioning marks that are printed on the carrier tape. Printing on the carrier tape is an additional manufacturing step, which increases the complexity of the manufacturing process and the cost. As cassettes are a consumable it is desirable to minimise their cost for the benefit of users and producers. In order to read the positioning marks, the carrier tape needs to be scanned by an optical reader. This has the disadvantage of adding to the cost of the device as well as it's power consumption. U.S. Pat. No. 8,282,893 B2 Schosnig et al. further develops this positioning system.

OBJECT

It is an object of the invention to provide an alternative tape positioning system and/or a method of positioning a tape.

SUMMARY

In one aspect, there is provided a method of positioning a tape that includes determining an estimated position of a test element on the tape and rotating a spool that carries the tape in order for the test element to be positioned at a reading station, wherein the estimated position of the test element is determined based on detected rotation of the spool, which can be measured at any shaft in the drive train.

In one embodiment, the method includes applying an algorithm with input variables based on revolutions of the spool and/or thickness of the tape.

In another embodiment, the method includes using a data set to correlate the rotation with the estimated position.

In another embodiment, the method includes reading the data set from a memory storage associated with a tape cassette that houses the spool and tape.

In another embodiment, the method includes reading historic data to identify a current location of the tape when loaded into an analyser.

In one embodiment, the method includes calibration of the estimated position by sensing the location of the test element.

In one embodiment, the method includes assessing when the estimated position of the test element is at or adjacent the reading station and activating a sensor to detect the location of the test element.

In one embodiment, the method includes detecting the location of the test element by identifying a leading or trailing edge of the test zone.

In one embodiment, the calibration includes rotating the spool by an additional increment to compensate for any difference between the estimated position and the detected location of the test element.

In one embodiment, the method includes providing an audible or visual indication for the required additional increment of winding needed for a manually wound cassette.

In one embodiment, the method includes using a sensor to locate the test element that is also used to analyse a sample on the test element.

In one embodiment, the method includes scrolling the test element into a storage chamber of the cassette after sample analysis is complete and writing an updated tape position to the memory storage.

In another aspect there is provided a testing process for testing a sample deposited on a test element of a tape held on a spool of a cassette, wherein the estimated position of the test element is determined based on rotation of the spool and the process includes calibrating the estimated position by activating an optic sensor to detect a leading or trailing edge of the test element in order to confirm the location of the test element, applying the sample to the test element and analysing the sample.

In one embodiment, calibrating the estimated position includes incrementally adjusting rotation of the spool to accommodate any difference between the estimated position of the test element with the actual position determined by the sensor.

In one embodiment, the process includes analysing the sample using the same sensor used to calibrate the estimated position of the test element.

In one embodiment, the process includes deactivating the sensor after the sensor analyses the sample.

In one embodiment, the process includes determining the estimated tape position using an algorithm based on the spool rotation and tape thickness.

In another embodiment, the process includes reading a data set associated with the tape cassette that provides a correlation between the spool rotation and estimated position of the test element.

In one embodiment, the process includes reading historic tape position data to determine the current estimated location of the test element.

In one embodiment, the process includes winding the test element with the analysed sample into a storage chamber of a cassette and writing a resultant tape position to a storage medium associated with the cassette.

In another aspect, there is provided a system for determining an estimated position of a test element on a tape which is carried by a cassette that has a spool which is rotated in order for the test element to be moved to a reading station, the system including an analyser with a bay for the cassette, a detector to monitor rotation of the spool and a processor to determine an estimated position of the test element based on the detected spool rotation.

In one embodiment, the system includes an optic sensor to analyse a sample deposited on the test element and to detect the actual position of the test element prior to testing, in order to calibrate the estimated position.

In one embodiment, the system includes a visual or audible indicator to prompt a user to incrementally wind the spool in the event calibration of the estimated position of the test element is needed.

In one embodiment, the system includes a storage medium that contains a data set associated with the cassette, which identifies the estimated position of the test element relative to the shaft rotation.

In one embodiment, the system includes a rotational marker which rotates in unison with the spool, the marker having one or more magnetic poles that electromagnetically interact with the detector to indicate the rotational position of the spool.

In another aspect, there is provided a memory storage medium associated with an in vitro diagnostic test cassette that has a spool which carries a tape with a series of test elements, the storage medium including a data set representing an estimated position of a test element relative to the rotational position of the spool.

In one embodiment, the storage medium includes tape position information which is updated after a sample is analysed on the test element and the test element is wound into a storage chamber of the cassette.

BRIEF DESCRIPTION OF THE DRAWINGS

The invention is described, by way of non-limiting example only, with reference to the accompanying drawings, in which.

DETAILED DESCRIPTION

Figure 1:
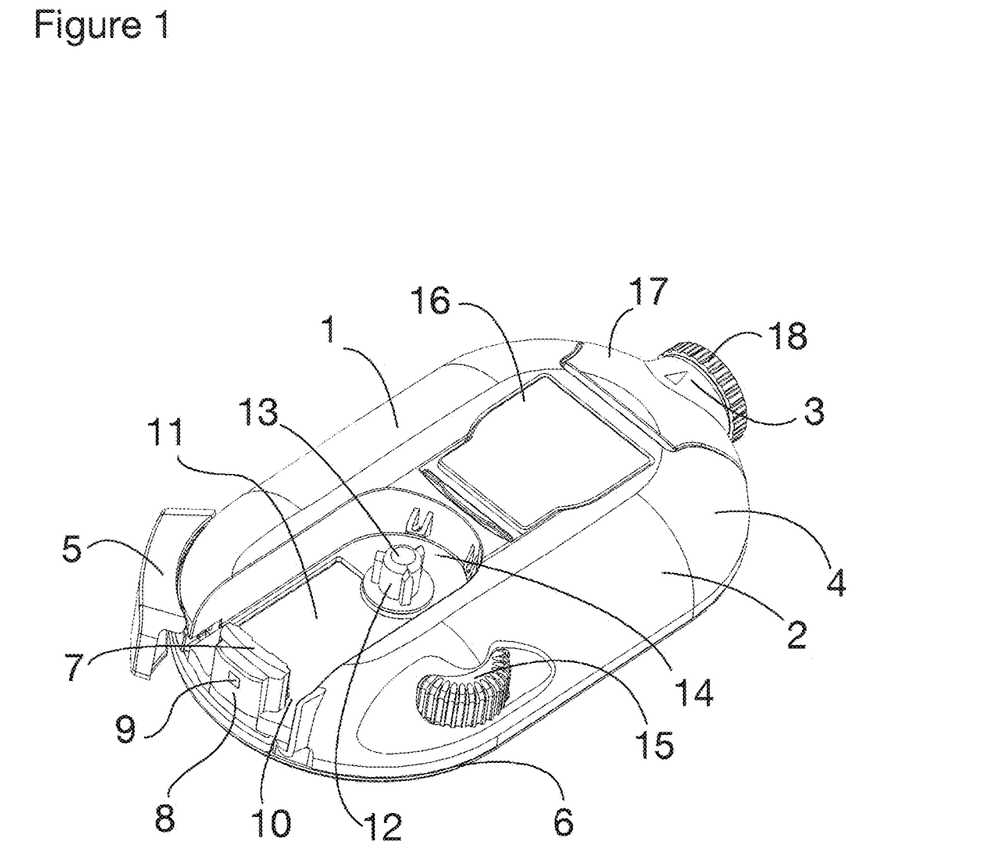
FIG. 1 is a perspective view of an analyser.

FIG. 1 shows an analyser 1 that includes a housing 2 with a lancing device 3 at one end 4 and a sliding cover 5 at an opposite end 6 that closes over a testing/reading station 7. The reading station 7 has a test head 8 and an optic sensor 9.

The reading station 7 is located at a forward end 10 of a bay 11. A take up drive 12 with a drive shaft 13 is positioned at a rear end 14 of the bay 11. The analyser 1 includes thumb wheel 15 that is used to turn the take up drive 12.

A battery compartment hatch 16 is provided intermediate the bay 11 and the lancing device 3. The lancing device 3 includes a hinged lancet cover 17 over a disposable lancet (not shown). The lancet cover 17 includes a depth adjustment dial 18 that is rotationally adjusted to change the firing distance of the lancet.

The lancing device 3 is be used to prick a finger or the like to generate a blood sample for testing.

Figure 2:
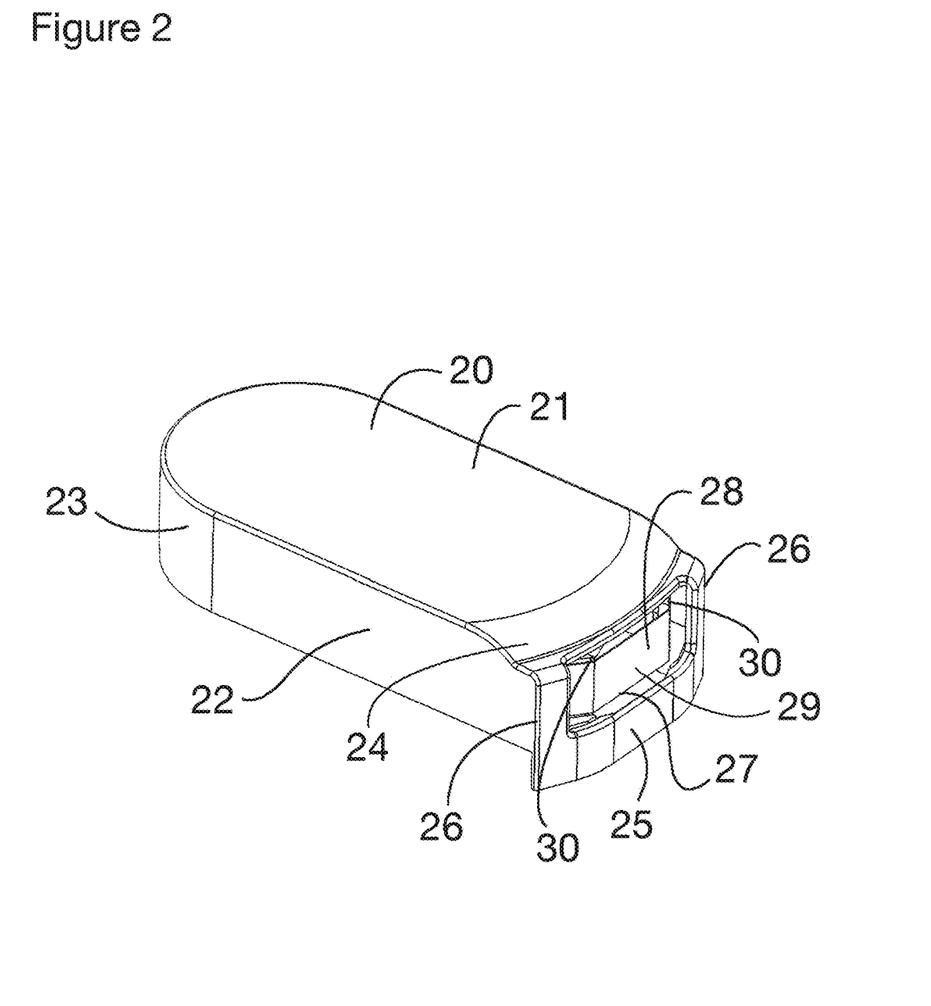
FIG. 2 is a perspective view of a cassette.

FIG. 2 shows a test cassette 20 that includes a body 21 shaped to fit in the bay 11 of the analyser 1 of FIG. 1. The cassette 20 has a generally rectangular main section 22 with a curved end 23 and a front section 24.

The front section 24 has a protective bar 25 with side arms 26 that position that bar 25 in alignment with a side edge 27 of a tape 28. The bar 25 and the arms 26 define a window 29 that allows a blood sample to be deposited on the tape 28. The tape 28 is tensioned over ramps 30 that are positioned inside the window 29.

When the cassette 20 is loaded into the device 1 of FIG. 1, the bar 25 is marginally displaced in a forward direction over the reading station 7 to allow the tape 28 to laterally slide into a testing position over the sensor 9.

Figure 3:
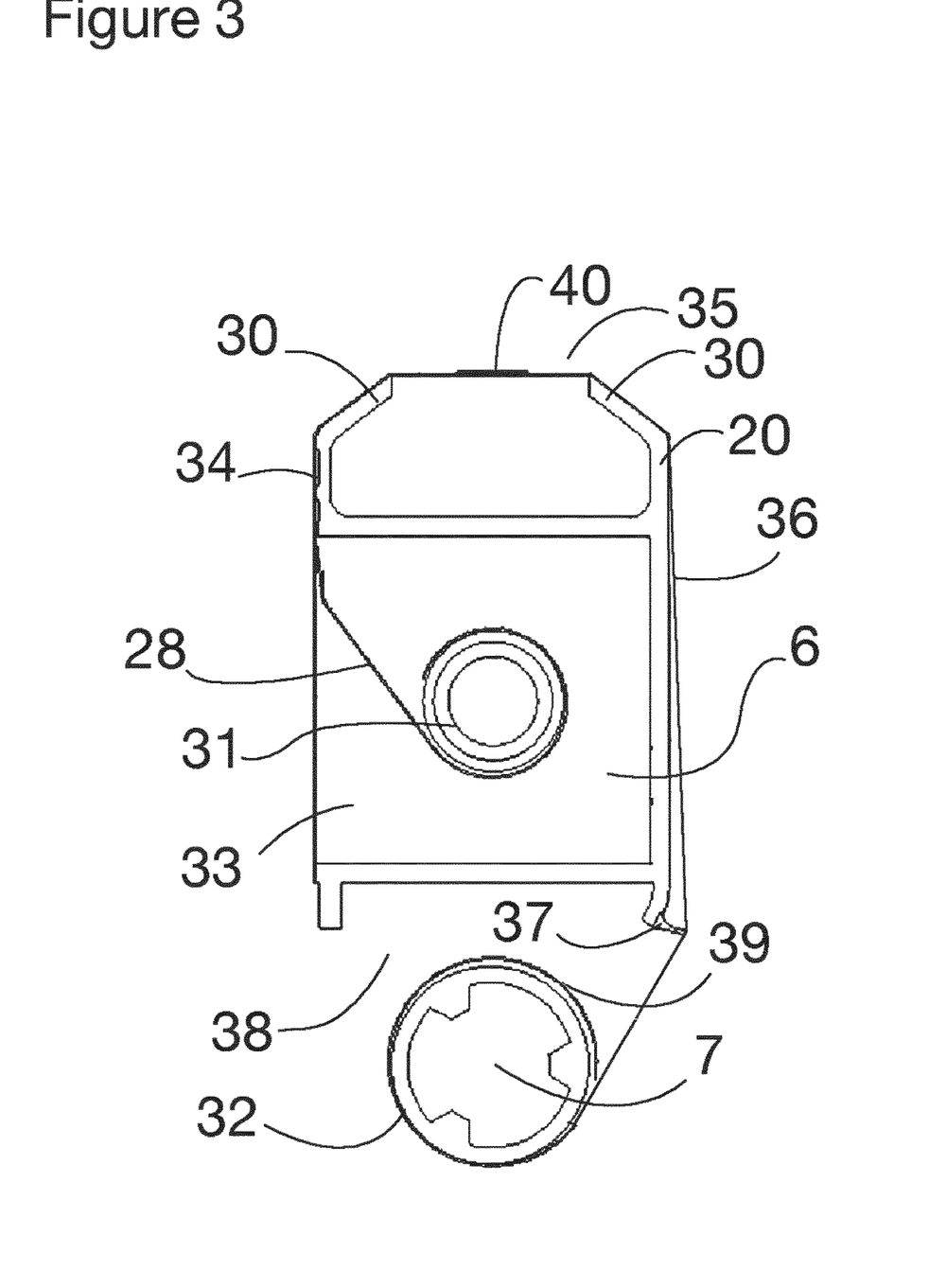
FIG. 3 is a diagrammatic internal plan view of the cassette.

FIG. 3 shows a diagrammatic view of the internal structure of the cassette 20, which includes a supply spool 31 and a take-up spool 32. The supply spool 31 is located in a storage chamber 33 and carries the tape 28 which is pulled out of the chamber 33 through a seal assembly 34 and across a gap 35 defined between the ramps 30. On the other side of the ramps 30, the tape 28 follows a path down the side 36 of the cassette 20, over a tensioning finger 37 and onto the uptake spool 32, which is located in a waste chamber 38.

The tape 28 is illustrated as being partially wound onto the take-up spool 32 to form a reel of tape 39. The positioning of the tape 28 is such that a test element 40 is positioned mid-way between the ramps 30. Multiple test elements 40 are provided along the length of the tape 28. This position of test element 40 corresponds to the element 40 being located over the reading station 7 when the cassette 20 is loaded into the bay 11 of the analyser 1 shown in FIG. 1.

Figure 4:
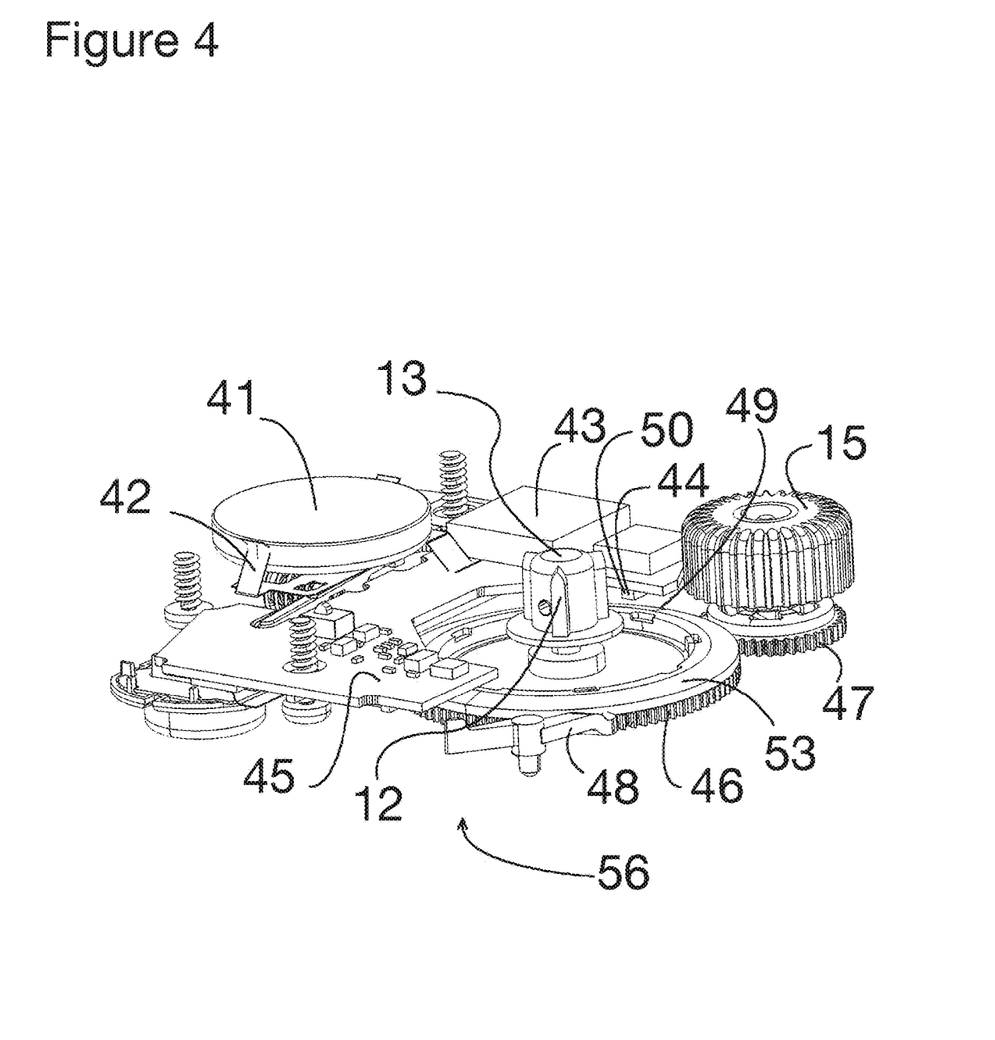
FIG. 4 is illustrates internal components of the analyser.

FIG. 4 shows internal components of the analyser 1. The components include a battery 41 with contacts 42, a microprocessor 43 and a detection device 50 in the form of a hall-effect sensor 44 fixed to a circuit board 45. A drive gear 46 is also provided to rotate the shaft 13 of the take up drive 12 of FIG. 1. The drive gear 46 is coupled to the thumb wheel 15 via a reduction gear 47 and a locking lever 48 is provided to lock and release the drive gear 46, as required. A multipolar ring magnet 53 is attached to the drive gear 46 and acts as a rotary marker 49 to indicate the rotational position of the gear 46.

Figure 5:
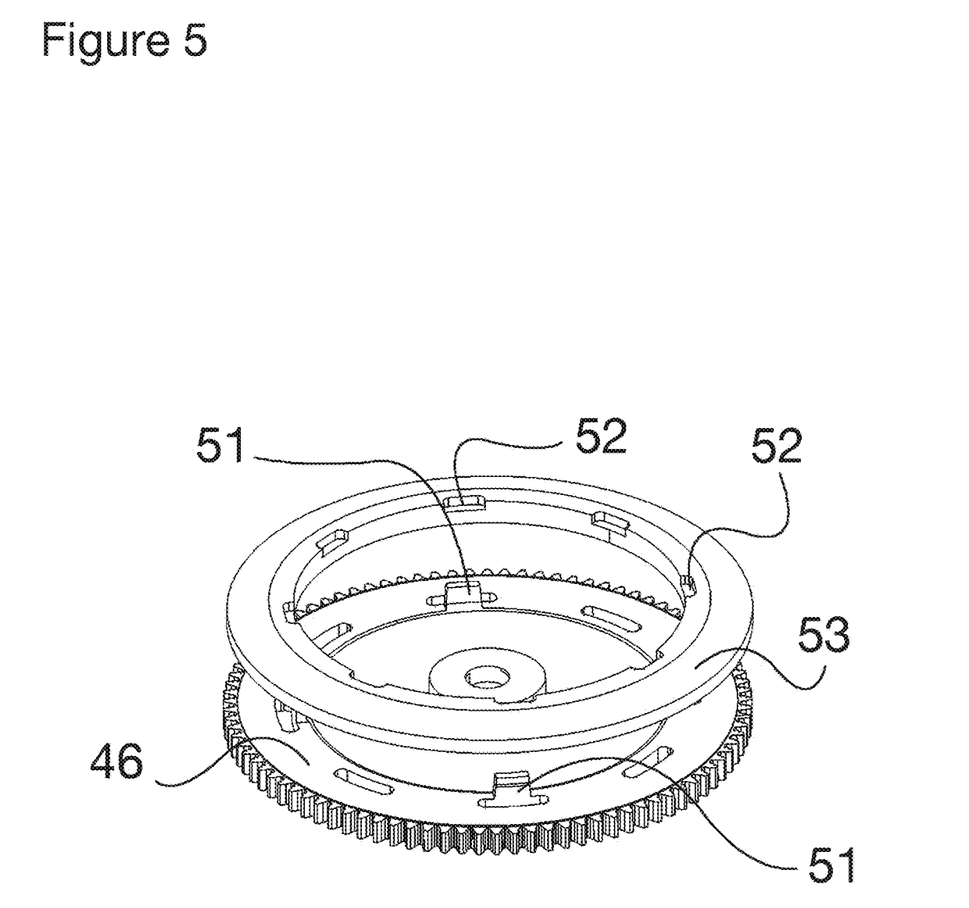
FIG. 5 is a perspective view of a drive gear of the analyser.

FIG. 5 shows the drive gear 46 with integrated retaining clips 51 snap-fitting with corresponding rebates 52 formed in the magnet 53.

Figure 6:
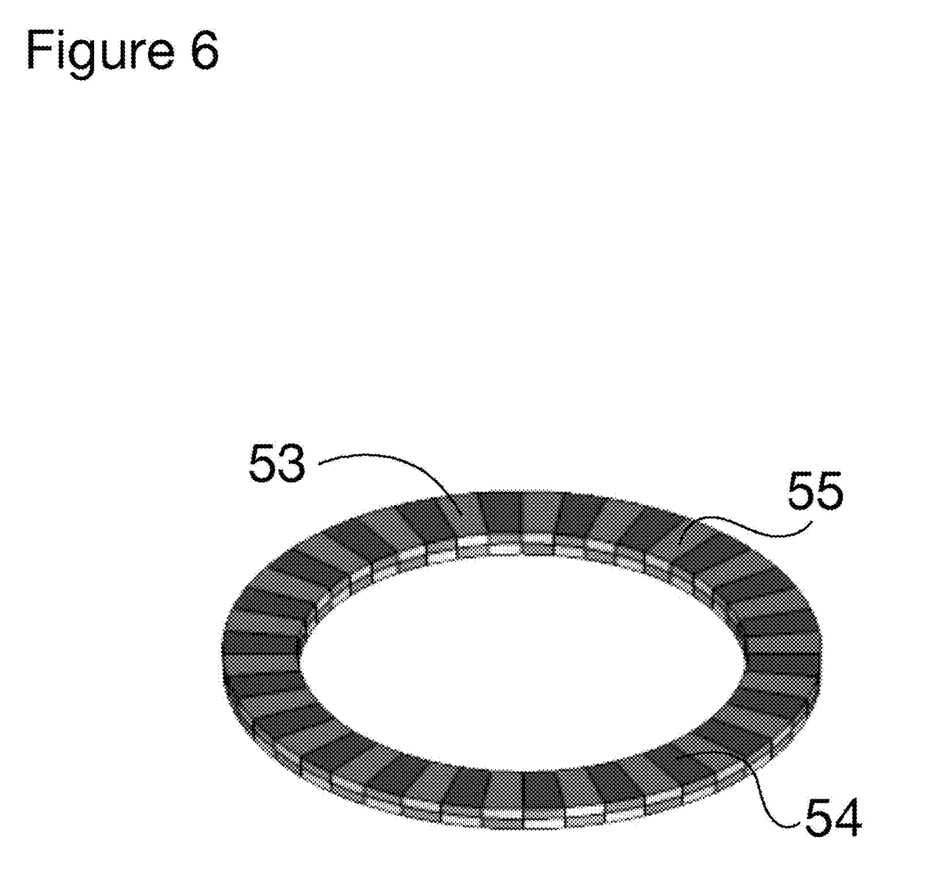
FIG. 6 is a perspective view of a ring magnet.

FIG. 6 illustrates the lay out of the poles in a multipolar ring magnet 53. North 54 and south 55 poles alternate around the magnet which moves in unison with the gear 46. Referring again to FIG. 4, the hall-effect sensor 44 monitors the rotation of the gear 46 by sensing electromagnetic pulses as the ring magnet 53 rotates. In that manner, the corresponding rotation of the spool 32 in the cassette 20 of FIG. 3 can be measured, which provides an indication of the length of tape 28 wound onto the spool 32 and allows the estimated position of the test element 40 to be calculated.

By having a relatively large gear 46 it is possible to house a large ring magnet 53. This increases the area for poles. In addition to this, by increasing the number of poles for example to 44 or 72 or more, it is possible to increase the resolution of positioning information relating to the positioning of the tape 28. This provides very accurate information on the location of the test elements 40. It also allows very small movements of the tape 28 to be detected.

The preferred form of marker 49 is a ring magnet as shown, however, other types of position indicating markers can instead be used, as appropriate. For example the gear 46 may have alternating black and white marks around the rim that can be detected by an alternative form of detection device 50 such as an optical detector.

In any event, when the gear 46 is rotated more tape 28 is wound onto the spool 32 and as the amount of tape 28 of the spool 32 increases, any movement of the gear 46 will result in greater movement of the tape 28.

The tape 28 that is wound onto the spool 32 will not present a perfectly round reel for a number of reasons. The tape 28 is not flat as it is constructed of carrier tape 28 with test elements 40 affixed at set intervals. The thickness of each test element 40 causes a roll of tests to be irregular. In addition, used test elements vary in thickness, due to the different volumes of blood applied to them by the user. The tape 28 on the spool 32 will therefore be out of round.

It has also been observed that, as tape 28 accumulates on the spool 32, the position of test elements 40, either on top of preceding elements 40 or between preceding elements 40, further impacts on the roundness of the reel 39. An out of round take-up spool 32 means a calculation to estimate the position of the test element 40 will contain error.

Another source of error is variation in tape tension between cassettes, which will change the diameter of the reel 39 by influencing how tightly or loosely the reel is wound. Errors from these and other sources, accumulate as the tape is used.

Calibrating the estimated position of the test element 40 can be achieved by periodically confirming the actual position of the test element. This may be done by optically detecting the test elements 40. The same optic sensor 9 of the analyser 1 used to test samples deposited on the test elements 40 can be used to detect the test elements. The calibration can then be effected by winding the spool 32 to incrementally adjust the position of the tape, as required.

The sensor 9 and the detection device 50 can thereby be used in combination as part of an overall system 56 for determining the estimated position of the test element 40, which utilises optical detection of the actual position of the test element 40 for calibration.

One method of detecting the test elements 40 and positioning the tape 28 includes detecting a leading or trailing edge of the test element. The tape position can be recalibrated and accumulated error thereby eliminated. In the case of a photochemical analyser, the optics used to measure the colour change of the test element, can also be used to detect the leading or trailing edge of the test element. In the case of an electrochemical analyser an optical sensor can be incorporated into the device. Since the magnetic sensor 44 can be used to identify the estimated position of the test element 40, an approximation can be made to determine when the leading or trailing edge of the test element 40 is near the optical sensor 9, such that the optical sensor 9 only needs to be activated to identify the position of the test element 40 and analyse the sample, after which the optical sensor 9 can be deactivated. The optical sensor 9 can be used very sparingly as a result, so as to reduce power consumption.

To determine an estimated position of the test element 40 based on the number of spool revolutions alone, a calculation may assume that a take up reel of initial diameter d, with n rotations, of tape of thickness t already wound, is absolutely circular. Therefore, with one complete turn it accumulates the equivalent length of tape dl, as a spool of fixed diameter $d+2*n*t$, or $dl=\pi*(d+2*n*t)$. For n rotations of the take up reel, (assuming perfect roundness), as the diameter shall be always variable, it is necessary to use the integral of $\pi*(d+2*n*t)$ for variable n, which can be expressed as $\pi*(d+2*n*t)dn$. This integrates to $l(n)=\pi*[d*n+t*n2]$. This formula gives the length of tape l(n) that a reel with diameter d, using tape of thickness t will accumulate in n rotations starting from zero rotations (n can also be a fraction of a rotation).

As an alternative to calculating the position of the test element 40 based on the above algorithm, the position of the tape 28 relative to the revolutions of the spool 32 can instead be empirically monitored and recorded for a standardized sample cassette, to develop a data set that includes information on the test element positions and the associated spool rotation.

Figure 7:
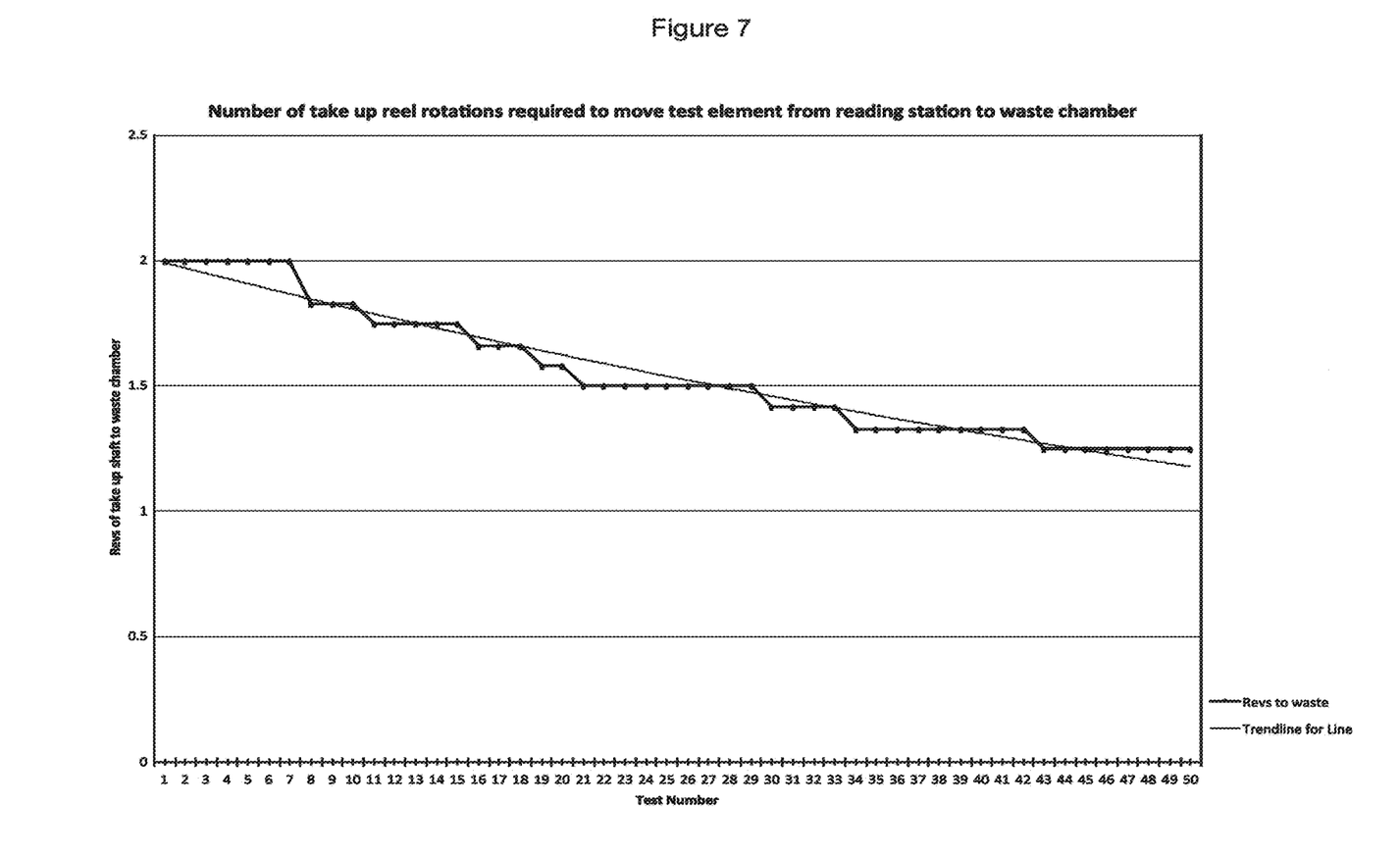
FIG. 7 is a plot of shaft rotations for positioning test elements.

FIG. 7 is a plot of actual shaft rotations required to move 50 consecutive test elements 40 from the reading station 7 to the waste chamber 38 of the cassette 20. Growth in the take-up reel 39 means fewer rotations are required as the test elements 40 are used.

The plot of FIG. 7 can be used to establish a data set, which represents the position of the test elements relative to the spool rotation. The cassette 20 can carry a suitable memory storage medium 58 for the data set, such as an RFID tag or the like, as illustrated in the system diagram of FIG. 8.

Figure 8:
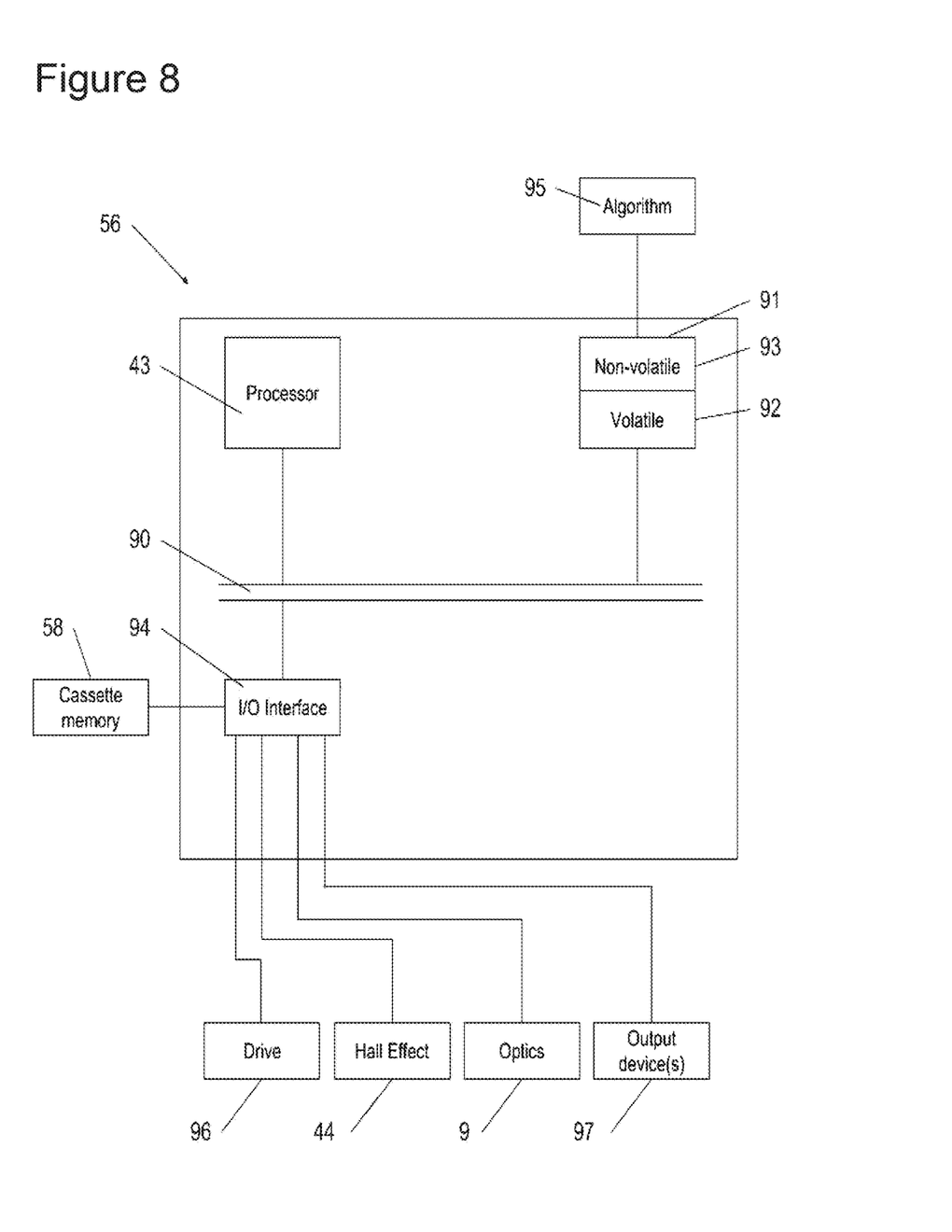
FIG. 8 is a system diagram.

FIG. 8 is a functional diagram of the overall system 56, which includes the processor 43 with a bus 90 that connects the processor to a memory 91 formed of volatile and non-volatile memory 92, 93.

The data set stored on the memory storage medium 58 can be accessed via an I/O interface 94 and used to determine an estimated position of the test element. As an alternative, an algorithm 95, such as described above, can be used to generate an estimated position of the test element in the volatile memory 92.

The processor 43 also interfaces with a drive 96 (in the case of an automated analyser 1), the hall-effect sensor 44, the optic sensor 9 and output devices 97, which provide an audio or visual output to signal the position of the test element and any additional winding that may be needed to move the test element to the reading station.

Figure 9:
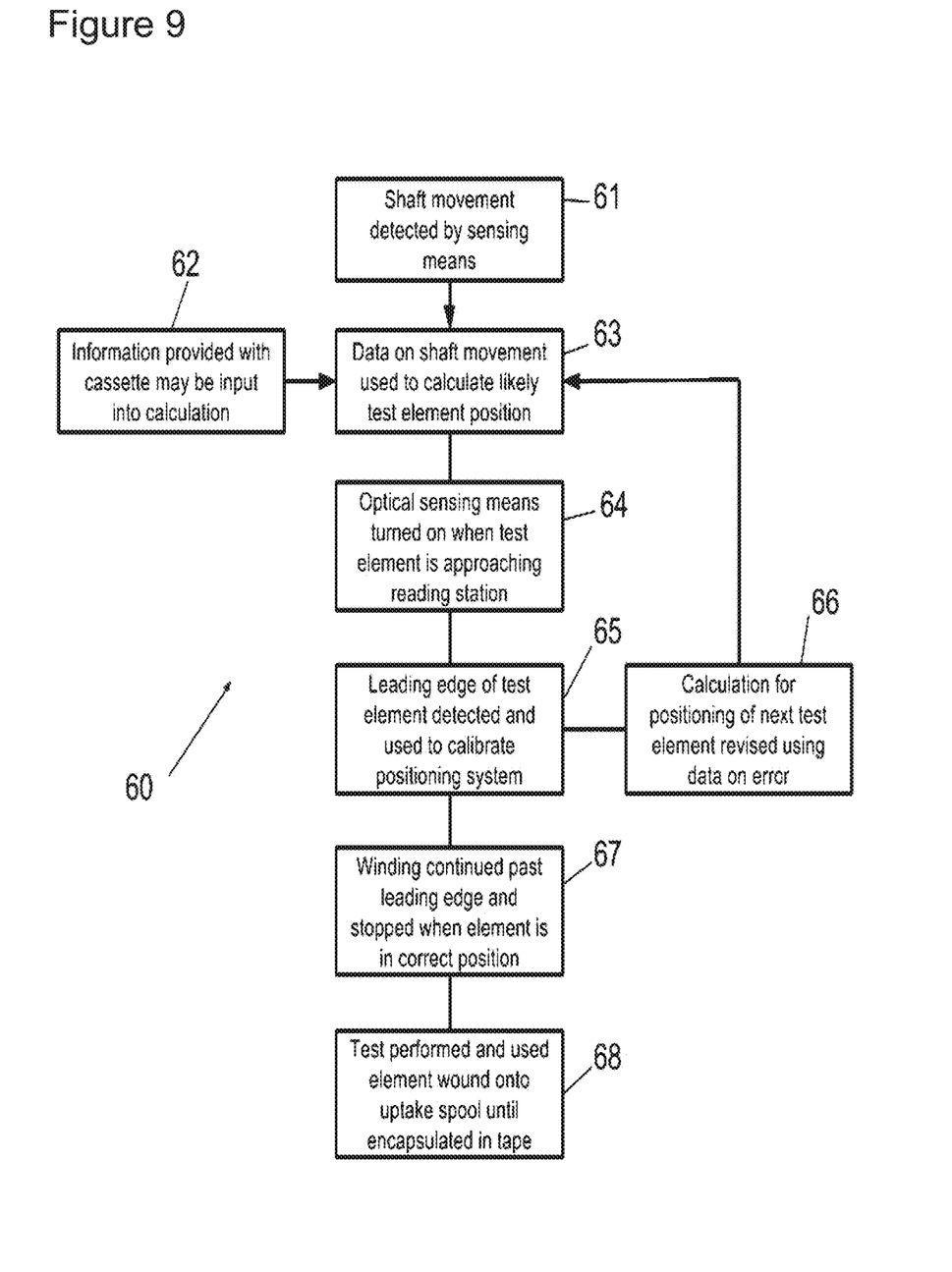
FIG. 9 is a flow chart illustrating a testing process.

Referring now to FIG. 9, a testing process 60 is illustrated, where initial rotation of the shaft 13 is detected by the hall-effect sensor 44 at step 61. Optional step 62 provides the data from the memory storage medium 58 to allow a calculation of the estimate position of the test element 40. The data set may optionally be programmed into the memory 91 of the analyser 1.

Based on the inputs at steps 61 and 62, an estimated position of the test element is determined at step 64. When the test element 40 is calculated to be adjacent the reading station 7, the optical sensor 9 is turned on at step 64 and a leading edge of the test element 40 is detected at step 65, which allows the test element position to be calibrated.

The calibration allows the estimated position of the next test element to be revised accordingly and that information is fed back into the calculation at step 66.

After calibration has been effected, the spool 32 is rotated further until the test element 40 is correctly positioned at the reading station, at step 67, where a blood sample or the like is deposited on the test element 40. A test or analysis is then performed and the tape 28 is further wound onto the spool 32 at step 68 until the used test element is covered by another layer of tape.

The estimated position of the test element 40 is recalibrated each time the leading edge of a test element 40 is detected by the optical sensor 9. If the prediction of when the leading edge is meant to be at the optical sensor 9 is incorrect, then corrections can likewise be made to correct the positioning error and the spool 32 incrementally adjusted accordingly. It is possible to use the trailing edge of the test element 40 for the calibration. Once testing and calibration is complete, the optic sensor 9 is turned off.

Figure 10:
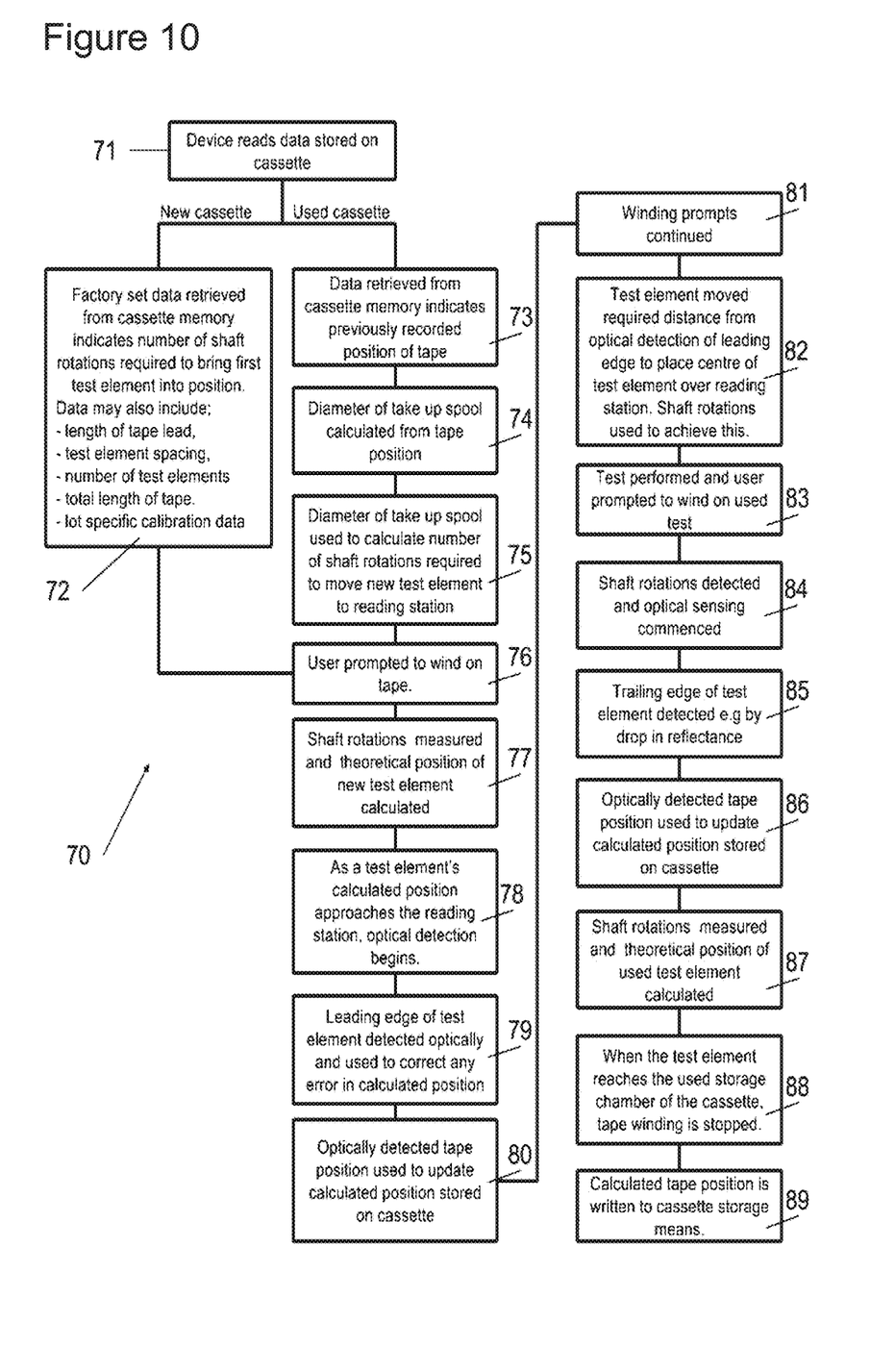
FIG. 10 is a flow chart illustrating another example of the testing process.

Referring now to FIG. 10, another testing process 70 is described that uses the same tape positioning method.

The process commences at step 71 with the analyser reading data stored in a data storage medium 58 on the cassette 20.

If the cassette is a new cassette, factory set data is retrieved at step 72 from the cassette memory 58 which indicates the number of shaft rotations required to bring the first test element 40 into position. The data may also include information such as the length of tape lead. The first test element 40 will be a set distance from the start of the tape 28. This distance or tape lead may optionally be programmed into the device or the distance may be stored on the cassette and read by the analyser 1. The information may also include data on the spacing between test elements 40, the number of test elements 40, the total length of tape 28 and lot specific calibration data.

Alternatively, if the cassette 20 has already been used, data is retrieved at step 73 from the cassette memory that indicates the previously recorded position of the tape 28.

A diameter of the take-up reel 39 can then be calculated from the tape position at step 74. The diameter of the take-up reel 39 can then be used to calculate the number of shaft rotations required to move a new test element 40 to the reading station 7, at step 75.

Once the estimated position of the test element 40 is determined, the processor 43 causes the output device 97 to generate a visual or audio signal to prompt a user to wind the tape 28, at step 76. Alternatively, a wind-on function may be performed automatically by the drive 96.

As the tape 28 is wound, the shaft rotations are measured at step 77 and a calculation is made at step 78 to determine when the test element 40 is at or adjacent the reading station 7 and the optical detector 9 is turned on.

A leading edge of the test element is then optically detected and used to correct any error in the estimated position of the test element 40 at step 79. The optically detected tape position is used to update the estimated position stored on the cassette at step 80.

After detecting the leading edge and calibrating the position of the test element 40, the user is again prompted to wind the tape at step 81. Again, this can also be done automatically.

The spool 32 is incrementally adjusted at step 82 for any required calibration so as to move the test element 40 into position, with the test element 40 centred over the optical sensor 9. In that position, a sample is applied to the test element 40 and a test or analysis is conducted using the optical sensor 9 at step 83, after which the user is again prompted to wind the tape 28 on to move the used test element 40 into the storage chamber 38.

When the spool 32 is rotated, the shaft rotations and the optic sensor 9 are monitored at step 84 to detect when a trailing edge of the test element 40 passes the testing station 7, at step 85.

The optically detected tape position is used to update the estimated position stored in the cassette's memory 58 at step 86. Once analysis and calibration is complete, the optic sensor 9 is de-activated.

The shaft rotations are again measured at step 87 as a result of signals received by the processor 43 through the interface 94, from the hall-effect sensor 44, to determine the estimated position when the used test element 40 is in the storage chamber, after which the tape winding is stopped, at step 88.

As a final step in the process, the estimated tape position is written to the cassette memory storage at step 89.

The invention provides a low cost, high resolution, reliable positioning system which overcomes the disadvantages of the prior art. This is achieved by measuring shaft revolutions and correcting any error by detecting the leading or trailing edge of the test elements 40. As such, there is no requirement for the tape to carry any markings to assist with tape positioning, aside from the test element itself, which reduces the cost and complexity of manufacture of the tape. Further, the activation of the optic sensor 9 only when needed for the purpose of calibration and testing, and the use of the same optic sensor 9 for both testing and calibration, minimises power consumption of the device 1.

In relation to the data set carried by the storage medium, additional data may be provided such as data on test element spacing, tape thickness and test thickness which can all be contained in an information storage means attached to each cassette 20. The analyser 1 may use this information in positioning calculations which account for the growth in diameter of the take-up spool and other patterns detected during use of the test cassette.

The information provided by the positioning system can be used to control a motor in the case of an automated analyser 1. In the case of manually driven tape, the user can be guided by the device's display and/or speaker/piezo buzzer. Graphics and sounds can alert the user that the test will soon be in position or is in position and that winding will soon need to stop or should stop.

Detecting very small movements of the tape provides the possibility of allowing users to test again using the same test element 40. This is only possible in the case of photochemical tests where the test element 40 is wider than needed in order to make it easier to align over the optical reader 9. If the positioning system has aligned the element so that only one half of it is used, then following the test, the element 40 could be moved so that the other unused half is over the optic sensor 9 ready for a repeat test. This small movement can be detected and the analyser programmed to run a fresh test. This would include assessing the unused test area to ensure it is usable. The second test would need to be performed within a prescribed period of time to ensure the test did not deteriorate due to exposure to the environment. Reasons for performing a second test can include, an error due to insufficient blood applied to the first test; a check of the first test because the result may seem implausible; failure of the first test due to user error, such as not washing hands before the test.

It should be appreciated the method has been described by specific reference to measuring the rotation of the shaft that drives the take-up spool. However, the measured shaft rotation may instead relate to the supply spool. In a similar context, the positioning of the test element is determined based on detected rotation of any shaft in the drive train, where the associated rotation of that shaft is able to be used to determine the estimated position of the test element and related calibration steps can be preformed in accordance with the above described methodology.

The invention claimed is:

1. A method of positioning a tape having a test element configured to react with a body fluid such that the test element is over a reading station where the body fluid is analysed, comprising:
    providing an apparatus including: a spool of the tape connected to a drivetrain, a first sensor, a second sensor, a processor, and the reading station;
    rotating the drivetrain;
    detecting, using the first sensor, a rotation of the spool by measuring the rotating of the drivetrain;
    determining, using the processor, an estimated position of the test element relative to the reading station by applying the detected rotation of the spool to an algorithm or data set representing a relationship between rotation of the spool and position of the test element;
    when the estimated position is not within a predetermined distance from the reading station, deactivating the second sensor;
    when the estimated position is within the predetermined distance from the reading station, activating the second sensor;
    detecting, using the second sensor, a position of the test element relative to the second sensor to verify the estimated position; and
    positioning the test element over the reading station so that the test element can be used to analyse the body fluid by rotating the spool an amount based on the estimated position.

2. The method of claim 1, further comprising:
    applying an algorithm with input variables based on revolutions of the spool or thickness of the tape in determining of the estimated position using the detected rotation of the spool.

3. The method of claim 1, further comprising:
    using a data set to correlate the detected rotation of the spool with the estimated position.

4. The method of claim 3, further comprising:
    reading the data set from a memory storage provided within a tape cassette that houses the spool.

5. The method of claim 4, further comprising:
    reading historic data to identify a current location of the tape when loaded into an analyser.

6. The method of claim 1, wherein detecting the position of the test element relative to the second sensor includes identifying a leading or trailing edge of the test element using the second sensor.

7. The method of claim 1, further comprising:
    calibrating the estimated position based on the detected position of the test element.

8. The method of claim 7, wherein the calibrating includes rotating the spool by an additional increment to compensate for any difference between the estimated position and the detected position of the test element.

9. The method of claim 8, further comprising:
    providing an audible or visual indication to prompt the additional increment of winding rotating needed for a manually wound cassette.

10. The method of claim 7, further comprising:
    using the second sensor to analyse the body fluid on the test element.

11. The method of claim 10, further comprising:
    moving the test element into a storage chamber of a cassette containing the spool by further rotating the drivetrain, after sample analysis is complete; and
    writing an updated tape position to a memory storage.

12. A testing process for testing a sample of body fluid deposited on a test element of a tape held on a spool of a cassette, the test element being configured to react with a body fluid, the process comprising:
    providing an apparatus including: the spool connected to a drivetrain, a first sensor, an optic sensor, a processor, and a reading station where the body fluid is analysed;
    rotating the drivetrain;
    detecting, using the first sensor, a rotation of the spool by measuring the rotating of the drivetrain;
    determining, using the processor, an estimated position of the test element relative to the reading station by applying the detected rotation of the spool to an algorithm or data set representing a relationship between rotation of the spool and position of the test element;
    when the estimated position is not within a predetermined distance from the reading station, deactivating the optic sensor;
    when the estimated position is within the predetermined distance from the reading station, activating the optic sensor;
    detecting, using the optic sensor, a position of a leading or trailing edge of the test element relative to the optic sensor;
    calibrating the estimated position by confirming it is equal to the position detected by the optic sensor; and applying the sample to the test element and analysing the sample.

13. The process of claim 12, wherein calibrating the estimated position includes incrementally adjusting rotation of the spool to accommodate any difference between the estimated position of the test element with the position detected by the optic sensor.

14. The process of claim 12, wherein the sample is analysed using the optic sensor.

15. The process of claim 14, further comprising:
deactivating the optic sensor after the optic sensor analyses the sample.

16. The process of claim 12, wherein determining the estimated position includes using an algorithm including spool rotation and tape thickness.

17. The process of claim 12, wherein determining of the estimated position includes reading a data set associated with the cassette that provides a correlation between spool rotation and the estimated position.

18. The process of claim 17, further comprising:
reading historic tape position data to identify a current position of the tape when loaded into an analyser.

19. The process of claim 12, further comprising:
moving the test element with the analysed sample into a storage chamber of the cassette by further rotating the drivetrain; and
writing a resultant tape position to a storage medium disposed within the cassette.

20. A system for determining an estimated position of a test element configured to react with a body fluid on a tape which is carried by a cassette that has a spool which is rotated for the test element to be moved to a reading station where the body fluid is analysed, the system comprising:
an analyser with a bay for the cassette;
a detector configured to detect rotation of the spool;
a processor configured to determine an estimated position of the test element relative to the reading station by applying the detected rotation of the spool to an algorithm or data set representing a relationship between rotation of the spool and position of the test element; and
an optic sensor configured to analyse a sample of body fluid deposited on the test element and to detect an actual position of the test element prior to testing, in order to calibrate the estimated position,
wherein the processor is further configured to deactivate the optic sensor when the estimated position is not within a predetermined distance from the reading station, and activate the optic sensor when the estimated position is within the predetermined distance from the reading station.

21. The system of claim 20, further comprising:
a visual or audible indicator configured to prompt a user to incrementally rotate the spool when calibration of the estimated position is needed.

22. The system of claim 20, further comprising:
a storage medium that contains a data set associated with the cassette, which identifies the estimated position of the test element relative to rotation of the spool.

23. The system of claim 20, further comprising:
a rotational marker which rotates in unison with the spool, the marker having one or more magnetic poles that electromagnetically interact with the detector to indicate a rotational position of the spool.

24. The system of claim 20, further comprising:
a storage medium including a data set representing the estimated position relative to rotational position of the spool.

25. The system of claim 24, wherein the storage medium includes tape position information which is updated after a sample is analysed on the test element and the test element is moved into a storage chamber of the cassette by further rotation of the spool.

* * * * *